(12) United States Patent  
Kumar (10) Patent No.: US 6,394,806 B1  
(45) Date of Patent: May 28, 2002

(54) SNAP-IN HEALING CAP

(75) Inventor: Ajay Kumar, Palmdale, CA (US)

(73) Assignee: Nobel Biocare USA, Inc, Yorba Linda, CA (US)

( * ) Notice: Subject to any disclaimer, the term of this patent is extended or adjusted under 35 U.S.C. 154(b) by 0 days.

(21) Appl. No.: 09/662,106

(22) Filed: Sep. 14, 2000

Related U.S. Application Data (60) Provisional application No. 60/153,843, filed on Sep. 14, 1999.

(51) Int. Cl.[7] .............................. A61C 8/00; A61C 3/00
(52) U.S. Cl. ........................................ 433/173; 433/141
(58) Field of Search ................................ 433/141, 172, 433/173, 174, 177

(56) References Cited

U.S. PATENT DOCUMENTS

| | | | |
|---|---|---|---|
| 4,836,781 A | * | 6/1989 | Meinershagen ............. 433/141 |
| 4,856,994 A | | 8/1989 | Lazzara et al. ............. 433/173 |
| 5,195,891 A | | 3/1993 | Sule ............................ 433/173 |
| 5,417,570 A | | 5/1995 | Zuest et al. ................. 433/177 |
| 5,492,471 A | | 2/1996 | Singer ........................ 433/172 |
| 5,904,483 A | | 5/1999 | Wade .......................... 433/173 |
| 6,206,696 B1 | * | 3/2001 | Day ............................. 433/141 |

* cited by examiner

*Primary Examiner*—Cary E. O'Connor
(74) *Attorney, Agent, or Firm*—Knobbe, Martens, Olson & Bear, LLP (57) ABSTRACT

A healing cap is provided for covering of an implant installed in a patient's mouth. The healing cap comprises a proximal end and a distal end. The proximal end is adapted to be inserted within a coronal opening formed in the implant. The healing cap further includes resilient fingers for engaging corresponding surfaces formed within the coronal opening of the implant. The distal end of the healing cap can include an indentation for receiving a snapping portion of a removal tool.

43 Claims, 7 Drawing Sheets

SNAP-IN HEALING CAP

CROSS REFERENCE TO RELATED APPLICATIONS

The present application claims priority and benefit under 35 U.S.C. §119(e) of U.S. Provisional Patent Application Ser. No. 60/153,843, filed Sep. 14, 1999.

BACKGROUND OF THE INVENTION

1. Field of the Invention

This invention relates to methods and devices that are used in implant dentistry to replace a natural tooth with a prosthetic tooth. More particularly, the invention relates to an improved healing cap that covers a dental implant after stage one surgery.

2. Description of the Related Art

Implant dentistry involves the restoration of edentulous area(s) in a patient's mouth using artificial components, including typically an implant fixture or root and a prosthetic tooth and/or final abutment which is secured to the implant fixture. According to state of the art techniques, the process for restoring a tooth and its root is carried out generally in three stages.

Stage I involves implanting the dental implant fixture into the bone of a patient's jaw. The oral surgeon first accesses the patient's jawbone through the patient's gum tissue and removes any remains of the tooth to be replaced. Next, the specific site in the patient's jaw where the implant will be anchored is widened by drilling and/or reaming to accommodate the width of the dental implant fixture to be implanted. Then, the dental implant fixture is inserted into the hole in the jawbone, typically by screwing, although other techniques are known for introducing the implant in the jawbone.

The implant fixture itself is typically fabricated from commercially pure titanium or a titanium alloy. Such materials are known to produce osseointegration of the fixture with the patient's jawbone. The dental implant fixture also typically includes a hollow threaded bore through at least a portion of its body and extending out through its proximal end which is exposed through the crestal bone for receiving and supporting the final tooth prosthesis and/or various intermediate components or attachments.

After the implant is initially installed in the jawbone a temporary healing screw or healing cap, which is ordinarily made of a dental grade metal, is secured over the exposed proximal end in order to seal the internal born. The healing screw typically includes a threaded end, which is screwed into the internal bore of the implant. After the healing screw is in place, the surgeon sutures the gum over the implant to allow the implant site to heal and to allow desired osseointegration to occur. Complete osseointegration typically takes anywhere from four to ten months.

During stage II, the surgeon re-accesses the implant fixture by making an incision through the patient's gum tissues. The healing screw is then removed, exposing the proximal end of the implant. A mold or impression is then taken of the patient's mouth to accurately record the position and orientation of the implant within the mouth. This is used to create a plaster model or analogue of the mouth and/or the implant site and provides the information needed to fabricate the prosthetic replacement tooth and any required intermediate prosthetic components. Stage II is typically completed by attaching to the implant a temporary healing abutment or other transmucosal component to control the healing and growth of the patient's gum tissue around the implant site.

Stage III involves fabrication and placement of a cosmetic tooth prosthesis to the implant fixture. The plaster analogue provides laboratory technicians with a model of the patient's mouth, including the orientation of the implant fixture relative to the surrounding teeth. Based on this model, the technician constructs a final restoration. The final step in the restorative process is replacing the temporary healing abutment with the final restoration.

There are several recurring problems or difficulties associated with securing the healing screw or cap to the implant during stage one and with removing the healing screw or cap during stage two surgery. For example, screwing the healing screw into the implant during stage one is time consuming, difficult and requires a secondary tool such as a screwdriver. Moreover, because the healing screw is small, it is difficult to handle and may be accidentally dropped into the patient's mouth if adequate care is not taken. Unscrewing the healing screw from the implant during stage two also is time consuming, difficult and requires an additional tool such as a screwdriver. Furthermore, the healing screw also may be accidentally dropped into the patient's mouth as it is removed from the implant if adequate care is not taken.

It should be appreciated that a set of two or more teeth can be replaced using the same procedure outlined above. In such a case, a single implant supports two or more prosthetic teeth. The present invention applies equally to the replacement of one tooth or several teeth.

SUMMARY OF THE INVENTION

It is an objective of this invention to provide an improved dental implant and healing cap that enables a surgeon to quickly and simply attach the healing cap to the dental implant without the need for an additional tool. It is another object of this invention to provide a healing cap that is quickly and simply removed from the implant. It is yet another object of the invention to provide a healing cap made of an inexpensive injection-molded plastic or any bio-compatible material, such as, for example, titanium, stainless steel, ceramic, or any combination thereof.

In one embodiment, the present invention provides a healing cap for covering a top surface of an implant installed in a patient's jawbone. The healing cap comprises a proximal end and a distal end. The proximal end is configured with one or more resilient prongs adapted to be inserted into a coronal opening formed in the implant and to be snappingly engage and secure the healing cap to the implant.

In another embodiment, the present invention provides a healing cap for covering a top surface of an implant installed in a patient's jawbone. The healing cap comprises a first end adapted to be snappingly mated to the implant and comprises a second end adapted to completely cover the top surface of the implant.

In yet another embodiment, the present invention provides an a healing cap for covering a top surface of an implant installed in a patient's jawbone. The healing cap comprises a proximal end and a distal end. The proximal end is sized and adapted to be inserted within a coronal opening formed in the implant. The healing cap further comprising a resilient snap means for snappingly engaging corresponding surfaces formed within the coronal opening of the implant. The distal end comprising a cover portion adapted to cover the top surface of the implant.

In yet another embodiment the present invention provides a removal tool for removing a healing cap that is snappingly mated to a dental implant installed in a patient's mouth. The removal tool includes a handle and one or more prongs adapted to be matingly and snappingly received in an indentation of the healing cap.

In yet another embodiment the present invention provides a method of installing and removing a healing cap that covers a top surface of an implant installed in a patient's jawbone. A proximal end of the healing cap is inserted into a coronal opening of the implant until the proximal end snappingly engages and secures the healing cap to the implant by applying a latent downward force on the implant. A snapping portion of a removal tool is inserted into a top portion of the healing cap such that a first removal force, which is greater than a second removal force required to remove the healing cap from the implant, is required to remove the removal tool from the top portion. The healing cap is separated from the implant by moving the removal tool away from the implant.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments and obvious variations thereof are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other features of the invention will now be described with reference to the drawings of the preferred embodiments, which are intended to illustrate and not to limit the invention, and in which:

FIG. 8 A–C are partial cross-sectional time assembly views illustrating the healing cap of FIG. 4 being inserted into the implant;

FIG. 9 A and B are detail views of the healing cap in the snapping chamber of implant assembly;

FIG. 12 A–C are partial cross-sectional time assembly views illustrating the removal tool of FIG. 10 being inserted into the healing cap of FIG. 4, which is already inserted into the implant of FIG. 1;

DETAILED DESCRIPTION OF THE PREFERRED EMBODIMENTS

Figure 1:
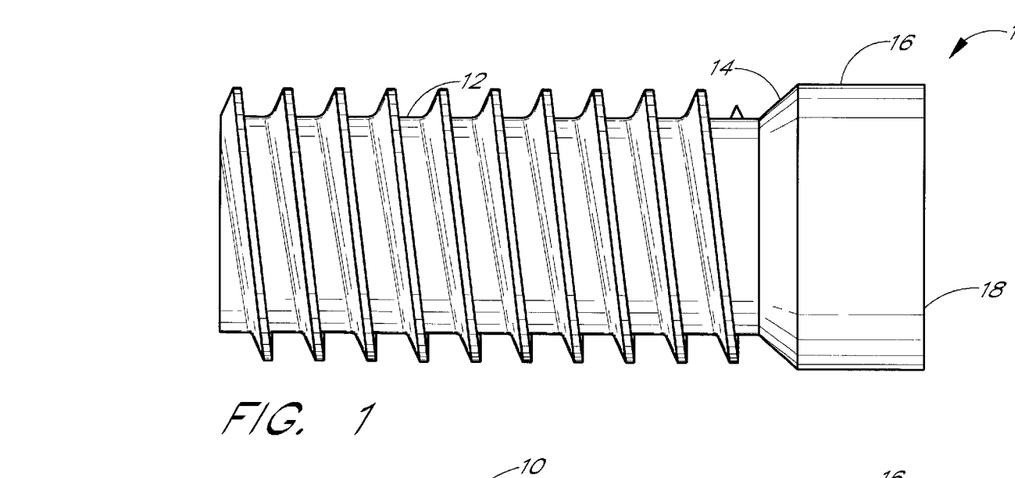
FIG. 1 is a side view of a dental implant having certain features and advantages according to the present invention.
Figure 2:
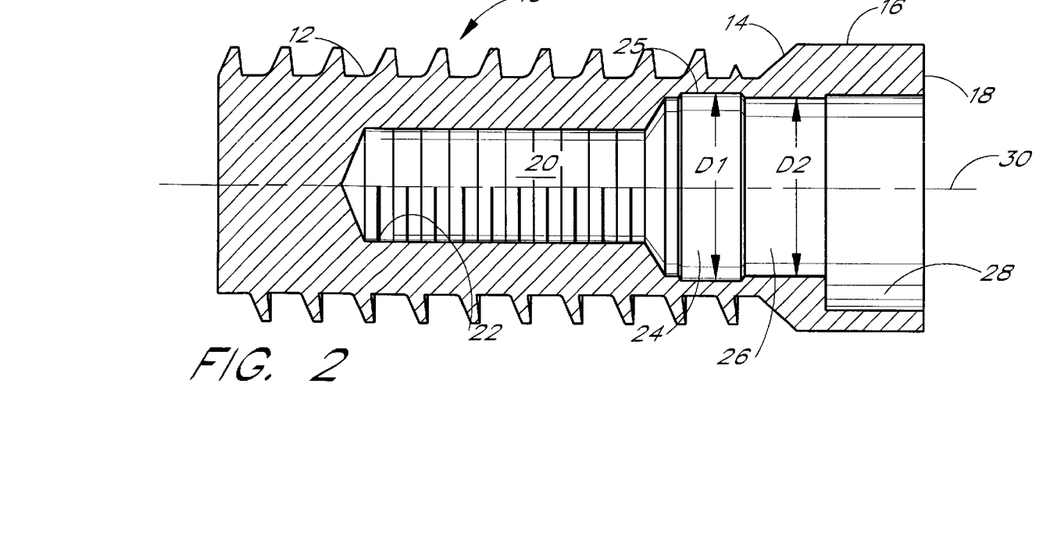
FIG. 2 is a cross-sectional view of the dental implant of FIG. 1 taken along line 2—2 of FIG. 3.
Figure 3:
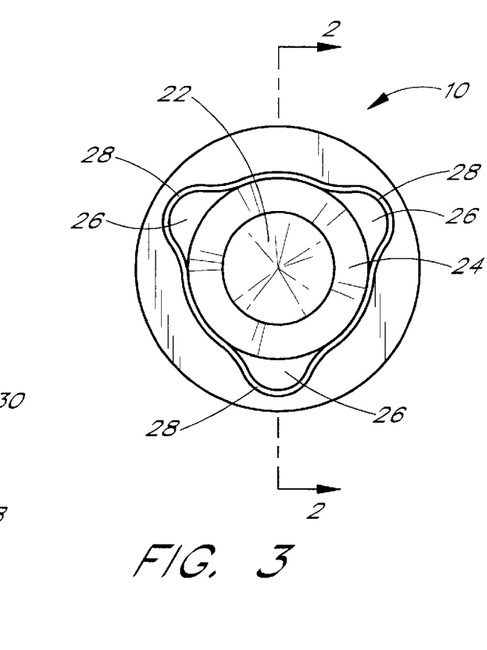
FIG. 3 is a top view of the dental implant of FIG. 1.
Figure 4:
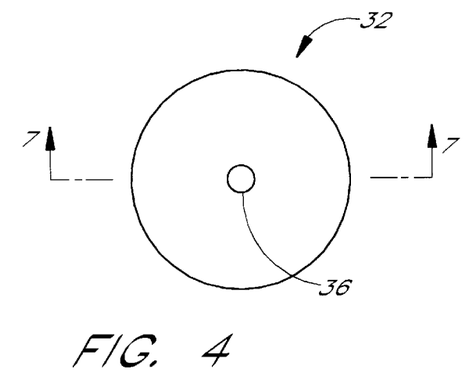
FIG. 4 is a top view of a healing cap having certain features and advantages according to the present invention.

FIGS. 1–3 illustrate a dental implant 10 particularly suited for receiving a snap-in healing cap having certain features and advantages according to one embodiment of the present invention. The implant 10 has an outer surface that is preferably divided into three regions: a body portion 12, a neck region 14, and a top portion 16. The body portion 12 preferably includes threads, and represents the portion of the implant 10 that is placed in either the mandible or the maxilla. As shown, the body portion 12 of the implant is substantially cylindrical or slightly tapered; however, the body portion 12 could also assume a conical shape or other known implant shapes, as desired. The threads of the body portion 12 preferably match preformed threads formed along the inner surface of an osteotomy formed in the patient's jawbone. However, the implant 10 could also be designed so as to be self-tapping. Preferably, the top portion 16 of the implant is substantially cylindrical and has a top surface 18 that is substantially flat.

As best seen in FIGS. 2 and 3, the implant 10 includes an inner cavity 20. The inner cavity 20 preferably includes a screw chamber 22, a snapping chamber 24, and an indexing chamber 26. Preferably, the diameter of the screw chamber 22 is smaller than the diameter of the snapping chamber 24. The snapping chamber 24 preferably includes a recess 25 that has an inner diameter D1 that is slightly larger than the diameter D2 of the indexing chamber 26.

The screw chamber 22 is preferably sized and configured so as to receive a bolt (not shown). The bolt can be used to temporarily or permanently attach a dental component, such as, for example, a temporary healing abutment or a final restoration to the implant 10. As will be described later, the snapping chamber 24 and the recess 25 are sized and configured to engage a corresponding snapping structure in a healing cap.

The indexing chamber 26 is best seen in FIGS. 2 and 3. In the illustrated arrangement, the indexing chamber 26 is substantially cylindrical with three lobes 28 that extend from the top surface 18 to the bottom of the indexing portion 26. The three lobes 28 are preferably substantially half circular in shape and are symmetrically situated around the perimeter of the indexing portion 26. Preferably, the center of each lobe 28 is about 120° apart from each other relative to a center axis 30 of the implant 10. It should be appreciated, however, that the indexing chamber 26 can be formed in a wide variety of other suitable symmetric or non-symmetric shapes that may be used with efficacy, giving due consideration to the goals of providing repeatable indexing and anti-rotation of mating components. For example, the indexing chamber 26 could comprise a hexagonal recess. In yet another arrangement, the implant 10 can include or protrusion (e.g., a hexagonal protrusion) that is situated on the top surface 18 of the implant 10. In which arrangements, the snapping chamber can be located closer to the top surface 18 of the implant 10 and the indexing chamber 26 can be eliminated. It should also be appreciated that the indexing chamber 26 is not a critical aspect of the present invention.

In fact, the present invention can be used with an implant 10 that does not include an indexing chamber 26.

FIGS. 4–7 illustrate one embodiment of a healing cap 32 having features and advantages in accordance with the present invention. The healing cap 32 is made of any bio-compatible material, such as, for example, an injection molded dental grade plastic, titanium, stainless steel, ceramics, and any combination thereof Preferably, the healing cap 32 is made of an inexpensive injection molded dental grade plastic because such a material is generally less expensive than metal and ceramic materials.

Figure 5:
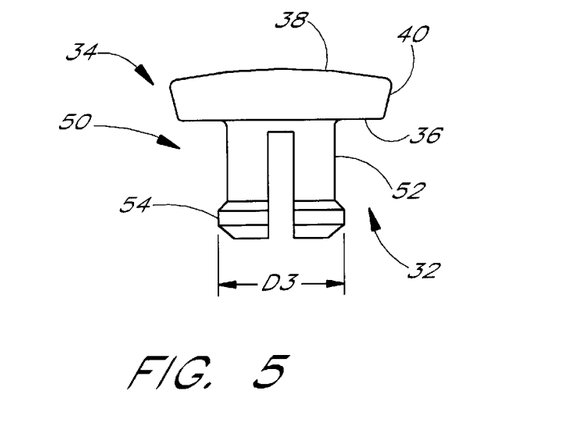
FIG. 5 is a side elevational view of the healing cap of FIG. 4.
Figure 6:
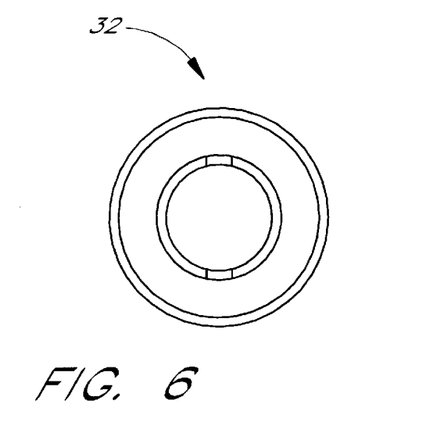
FIG. 6 is a bottom view of the healing cap of FIG. 4.
Figure 7:
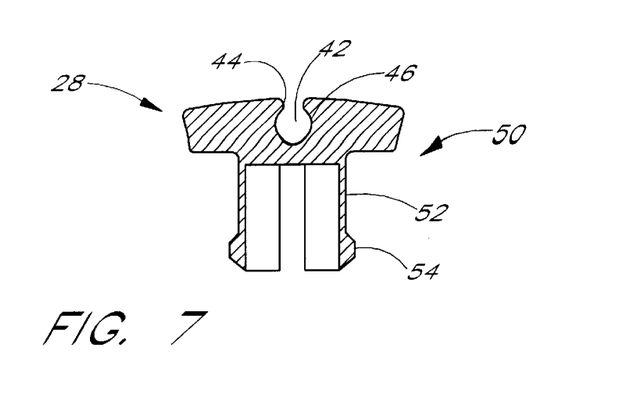
FIG. 7 is a cross-sectional view of the healing cap of FIG. 4 taken along line 7—7 of FIG. 4.

As best shown in FIGS. 5 and 7, the healing cap 32 has two main parts: a cover portion 34 and a snapping portion 50. The cover portion 34 has a substantially flat lower surface 36 that has a diameter that is approximately the same as the top surface 18 of the implant 10. The cover portion 34 also includes a top surface 38 that is substantially smooth and in the illustrated arrangement has a diameter slightly larger than the lower surface 36. In the illustrated arrangement, a side wall 40 connects the top surface 38 to the lower surface 36.

Preferably, the cover portion 34 also includes an indentation 42 which is desirably located near or at the center of the top surface 38. The indentation 42 includes a neck 44, which has a diameter that is smaller than a diameter of a lower portion 46 of the indentation 42. The function of the indentation 42 will be described in detail below.

The illustrated snapping portion 50 consists of a plurality of prongs or tangs 52. Each prong 52 preferably includes a protrusion 54. The protrusions 54 are preferably sized and configured to snap into and resiliently engage the snapping chamber 24 of the implant 10. Accordingly, the protrusions 54 have an outer diameter D3 that is preferably slightly larger than the inner diameter D1 of the indexing chamber 26 (see FIG. 2). Although in the illustrated arrangement the protrusions 54 are beveled (i.e., comprising two slanted sides and one flat side), it should be appreciated that the protrusions can also be fully or partially rounded as desired.

Figure 8A:
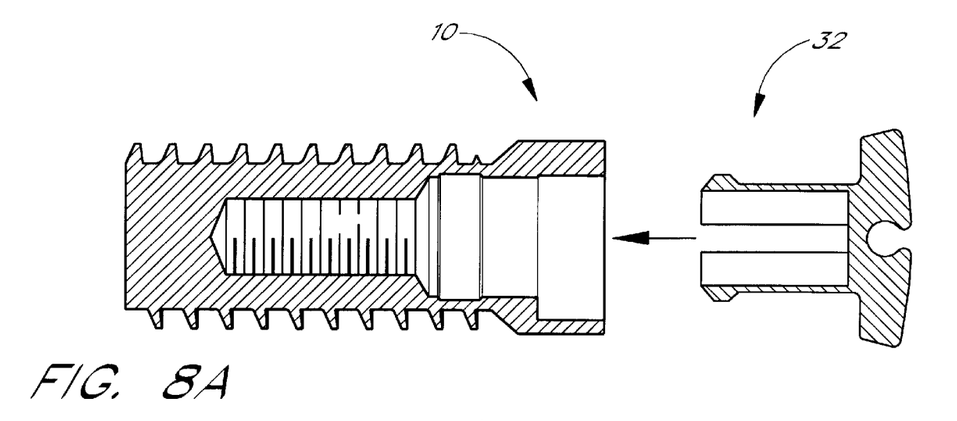
Figure 8B:
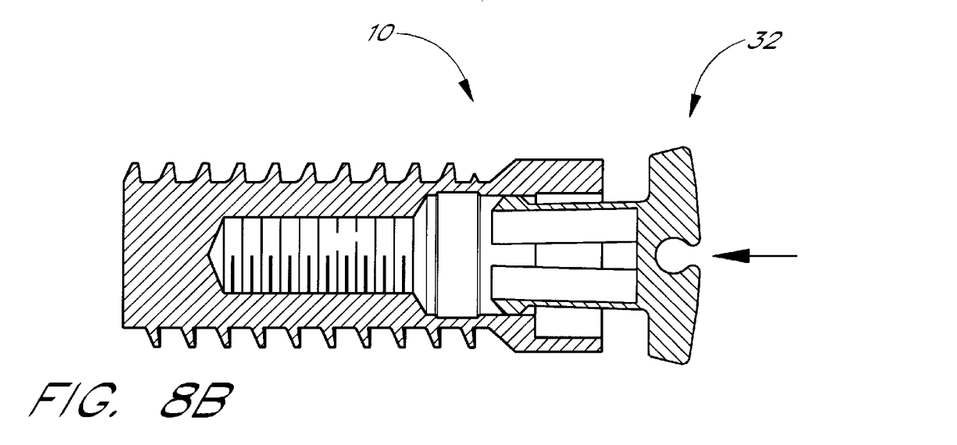
Figure 8C:
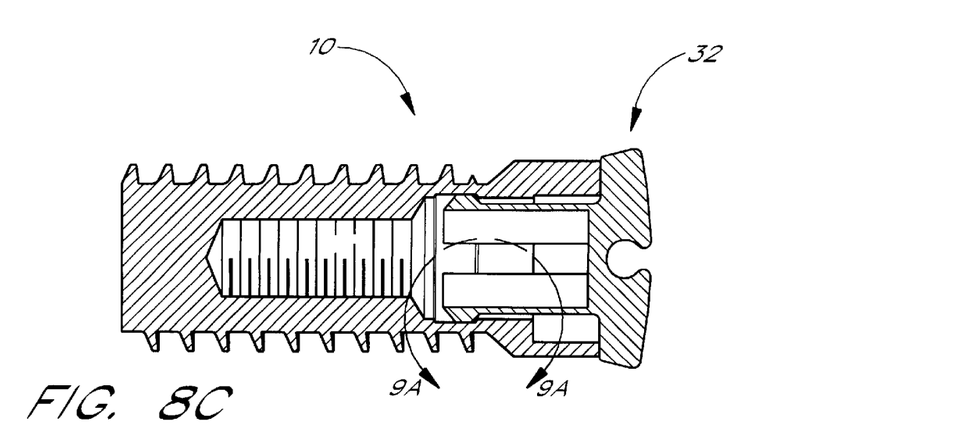
Figure 9A:
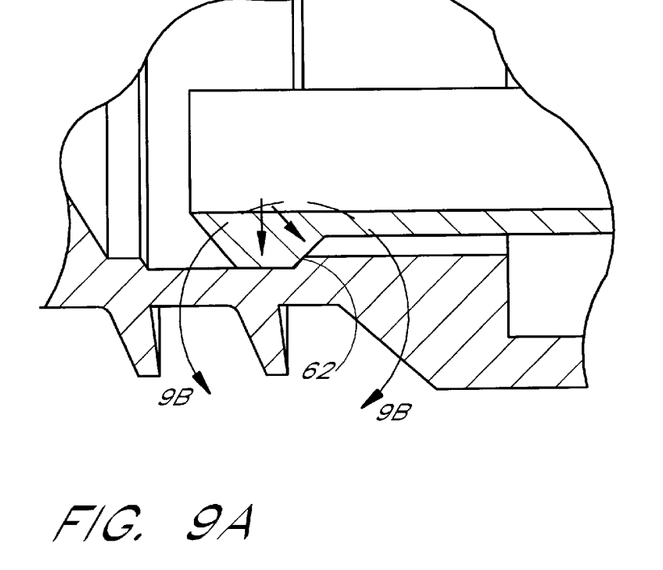
Figure 9B:
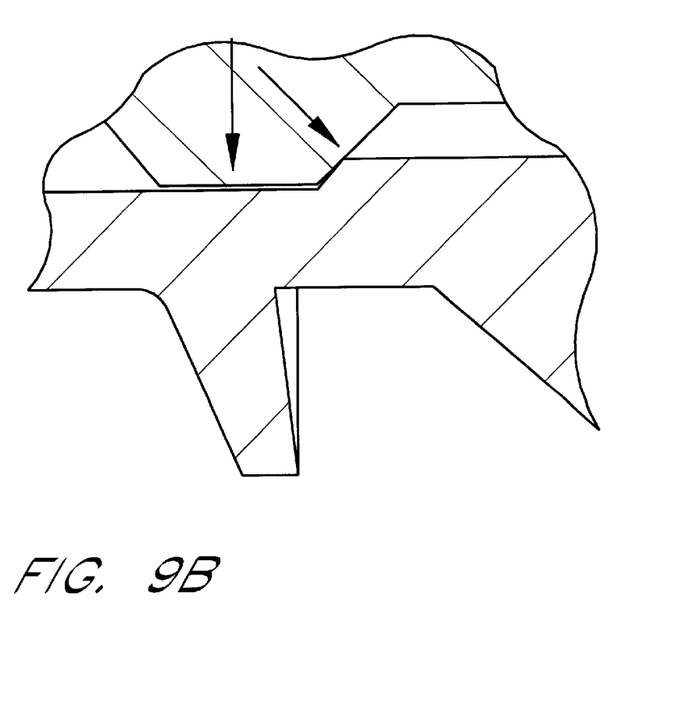

Referring to FIGS. 8 A–C, to attach the healing 32 to the implant 10 during stage I, the surgeon simply places healing cap 32 over the implant 10 and pushes the snapping portion 50 of the healing cap 32 into the implant 10, as will be described in more detail below. As mentioned above, the protrusions 54 of the healing cap 32 preferably, have at least a slightly larger diameter D3 than the inner diameter D2 of the indexing chamber 26. Accordingly, the snapping portion 50 of the healing cap 32 is compressed as it passes through the indexing chamber 26 (see FIG. 8A and B). Once the prongs 52 reach the snapping chamber 24, they partially expand forming a snap fit between the healing cap 32 and the implant 10 (see FIG. 8C). Additionally and advantageously, as the healing cap 32 is mated against the top surface 18 of the implant 10, the prongs 52 preferably resiliently engage a slanted inner surface 62 of the snapping chamber 22 (see FIG. 9A). Thus, the pressure exerted against the partially compressed prongs 52 by the slanted inner surface 62 of the snapping chamber 22 creates a reaction downward pulling force. This downward pulling force on the cap 32 causes the lower surface 36 of the healing cap 32 and the top surface 18 of the implant 10 to form a seal (see FIG. 8C). Advantageously, this prevents and/or minimizes leakage of saliva and bacterial contaminants into the implant 10 and thus prevents infection between stage I surgery and stage II surgery.

Clinically and advantageously, the dentist can be assured of the proper placement or seating of the healing cap 32 because as the healing cap 32 is pulled or urged down into the implant 10 the dentist can "feel" the snap fit and hear the audible "click" as the prongs 52 snap into the snapping chamber 24 of the implant 10. Additionally, the dentist may visually confirm that the healing cap 32 is properly placed or seated by viewing the lower surface 36 of the healing cap 32 and the top surface 18 of the implant 10 using a dental mirror. If desired, the proper placement or engagement of the healing cap 32 may be confirmed by attempting to remove the healing cap 32. A properly seated coping will have perceivable resistance to removal forces as the prongs 48 become compressed as they are pulled back into the indexing chamber 26 (see FIG. 8B).

Figure 10:
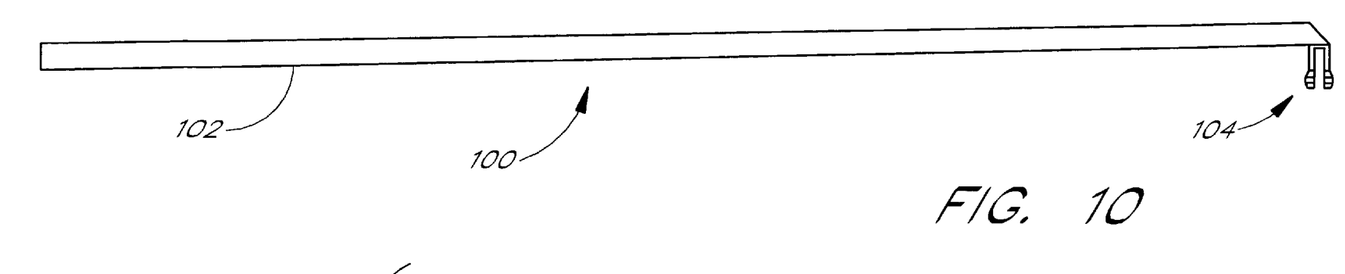
FIG. 10 is a side elevational view of a removal tool having certain fetures and advantages according to the present invention.
Figure 11:
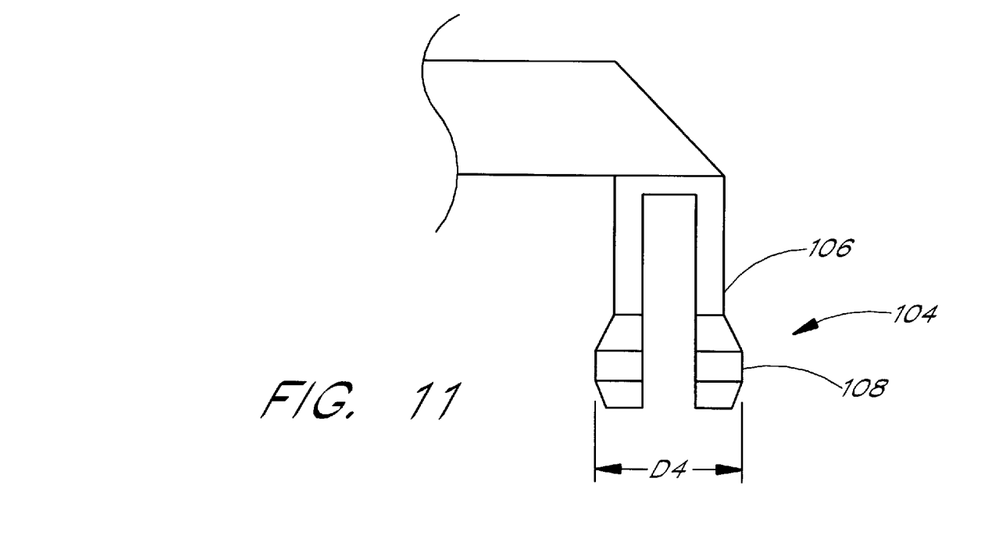
FIG. 11 is a close up view of the snapping portion of the removal tool of FIG. 10.

To remove the healing cap 32 during stage two, the surgeon may use a removal tool 100, which is depicted in FIGS. 10 and 11. The handle 100 preferably includes a stem 102 and a snapping portion 104. The snapping portion 104 is similar in shape and function as the snapping portion 40 of the healing cap 32. The main difference is that the snapping portion 104 of the removal tool 100 is configured to engage the indentation 42 on top of the healing cap 32 (FIG. 7) in a snap fit. Accordingly, the snapping portion 104 includes a plurality of prongs or tangs 106. Each prong 106 preferably includes a protrusion 108 that can be beveled (as illustrated) or rounded. As mentioned above, the protrusions 108 are preferably sized and configured to snap into and resiliently engage the indentation 42 of the healing cap 32 (see FIG. 7). Accordingly, the protrusions have an outer diameter D4 that is slightly larger than the diameter of the neck 44 of the indentation 42.

Figure 12A:
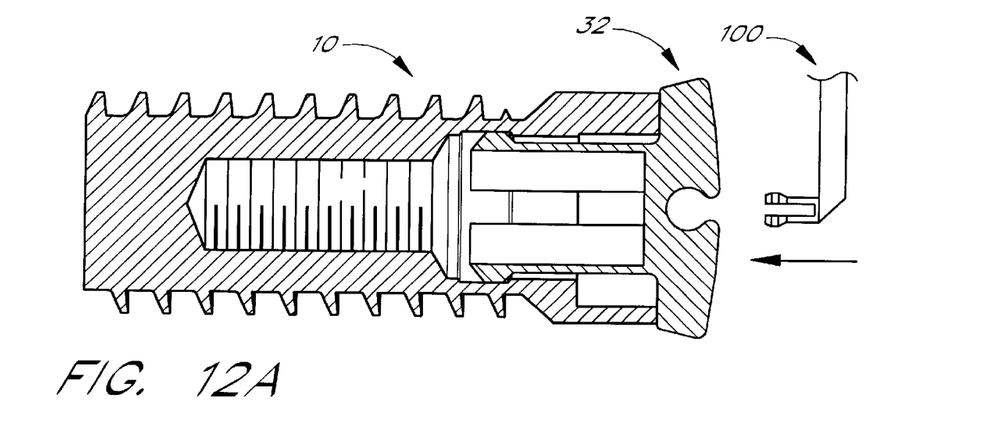
Figure 12B:
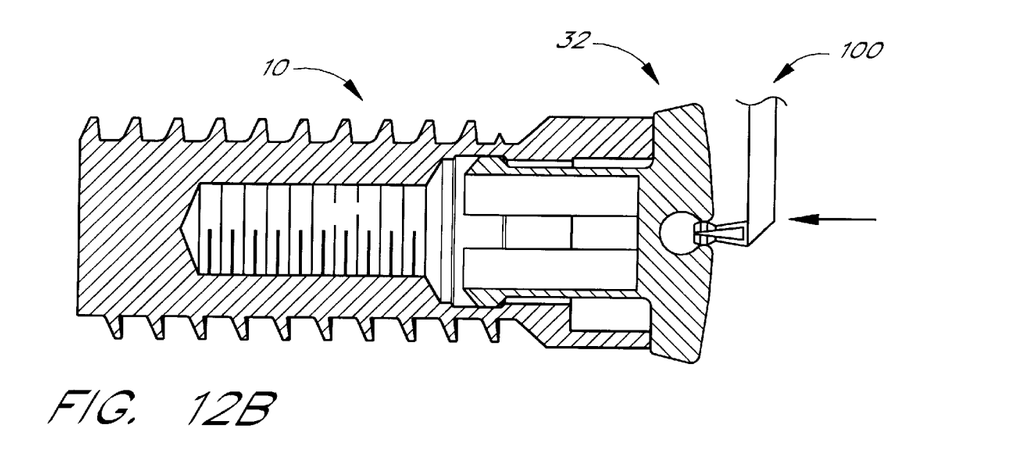
Figure 12C:
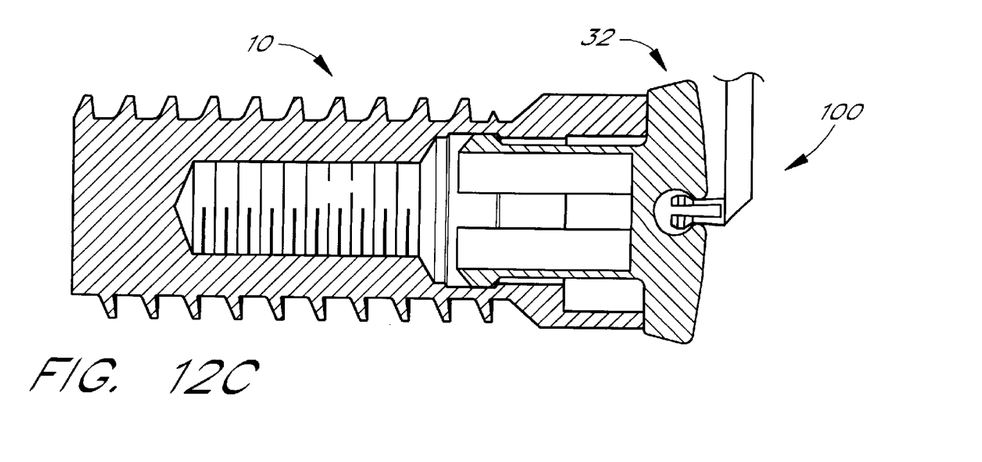

Referring to FIGS. 12A–B, to remove the healing cap 32 from the implant 10 during stage II, the dentist simply places the snapping portion 104 of the removal tool 100 over the indentation 42 and pushes the snapping portion 104 into the indentation 42. As mentioned above, the protrusions 108 of the handle 100 preferably, have at least a slightly larger diameter D4 than the neck 44 of the indentation 42. Accordingly, the snapping portion 104 of the handle 100 is compressed as it passes through the neck 44 (see FIG. 12B). Once the protrusions 108 reach the lower portion 46 of the indentation 42, the prongs 106 partially expand forming a snap fit between the handle 100 and the healing cap 32.

The handle 100 and heating cap 32 are preferably configured so that a force required to remove the healing cap 32 from the implant 10 is less than the force required to remove the handle 100 from the healing cap 32. Therefore, when the dentist lifts the removal tool 100 away from the implant 10, the healing cap 32 remains attached to the handle 100 but detaches from the implant 10.

The snapping forces between the healing cap 32, and the implant 10 are determined primarily by the outer diameter of the protrusions 54, the inner diameter of the recess 25, the inner diameter of the indexing chamber 26, and friction between contacting mated surfaces. Similarly, the snapping forces between the handle 100 and the healing cap 32 are determined primarily by the outer diameter D4 of the protrusions 108, the inner diameter of the lower potion 46, the inner diameter of the neck 44, the friction between contacting mating surfaces. To decrease the snapping force, the inner diameter of the protrusions 54, 108 can also be decreased while maintaining the inner diameters of the recess 25 and the indexing chamber 26 and the inner diameters of the lower portion 46 and neck 44. The snapping force may also be decreased or controlled by increasing the diameter of the indexing chamber 26 (or the neck 44) while maintaining the size of the protrusions 43 (or 108) and the recess 25 (or lower portion 46).

As mentioned above, the healing cap can be made of any bio-compatible material, such as, for example, dental grade plastic, titanium, stainless steel, ceramic, or any combination thereof. The healing cap 32 is preferably made of an injection molded dental grade plastic, which is particularly useful for forming the snapping portion 52 because of its resilient properties. Accordingly, in one arrangement of the present invention, the cover 34 of the healing cap 32 is made of a metal or ceramic material while the snapping portion 50 is made a plastic material.

If the healing cap 32 and/or the handle 100 and/or parts thereof are made of metal, such as, for example, Titanium or Stainless Steel, the surface of the protrusions 54, 108 may preferably be coated or otherwise treated with Teflon, diamond-like carbon coating (e.g. amorphous diamond), or titanium anodic coating, or any other lubricious coating capable of making the surfaces slide easier. See, for example, U.S. Pat. No. 5,833,463 incorporated herein by reference.

Figure 13:
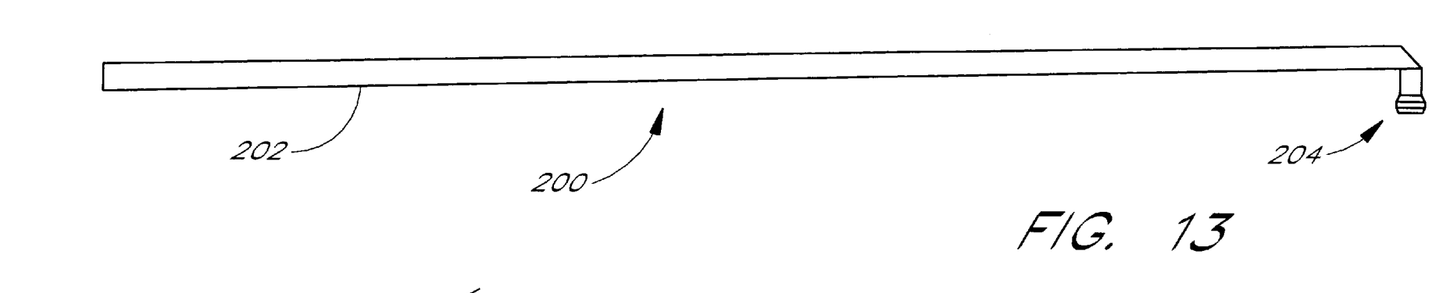
FIG. 13 is a modified arrangement of a removal tool having certain features and advantages according to the present invention.
Figure 14:
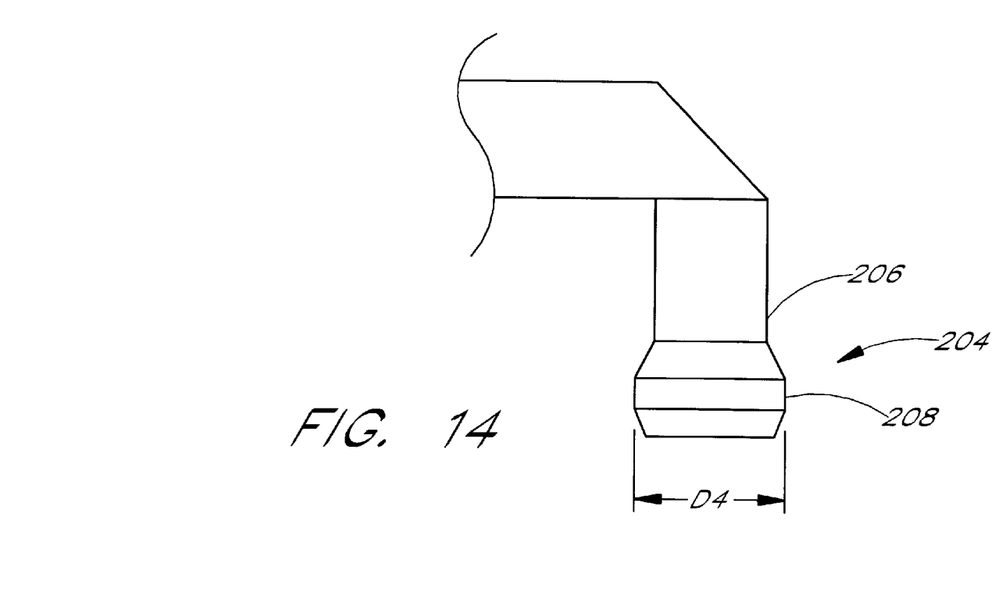
FIG. 14 a close up view of the snapping portion of the removal tool of FIG. 13

FIGS. 13 and 14 illustrate a modified arrangement of a removal tool 200. As with the previous arrangement, the removal tool 200 includes a handle 202 and a snapping portion 204. The snapping portion includes a prong 206 and a protrusion 208, which has a diameter D4 greater than the diameter of the neck 44 of the healing cap 32.

The main difference in this arrangement is that the snapping portion 204 is not resilient. Thus, to remove the healing cap 32 during stage II, the dentist places the snapping portion 204 of the removal tool 200 over the indentation 42 and pushes the snapping portion 204 into the indentation 42. As mentioned above, the protrusions 208 of the handle 200 preferably, have at least a slightly larger diameter D4 than the neck 44 of the indentation 42. Accordingly, the neck 44 is configured to deflect as the protrusion 208 passes through the neck 44. Once the protrusion 208 reach the lower portion 46 of the indentation 42, the neck 44 return to its original position thereby forming a snap lit between the handle 200 and the healing cap 32. In such an arrangement, the healing cap 32 is preferably made of plastic so that the neck is resilient.

It should also be noted that although in the illustrated embodiments the healing cap 32 is removed from the implant 10 by engaging a removal tool with the healing cap 32, the healing cap 32 can also be separated from the implant 10 by using a dental pick (not shown) or other conventional dental implement. Specifically, the dentist can use the dental pick or other implement to pry the healing cap 32 away from the implant 10. In such an arrangement, the healing cap 32 preferably does not include the indentation 42.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A healing cap for covering a top surface of an implant installed in a patient's jawbone, the healing cap comprising a proximal end and a distal end, said proximal end being configured with one or more resilient prongs adapted to be inserted into a coronal opening formed in said implant and to snappingly engage and secure said healing cap to said implant, wherein said distal end includes an indentation having a neck with a diameter smaller than a diameter of a lower portion of said indentation.

2. The impression healing cap of claim 1, wherein one or more of said resilient prongs comprises one or more protrusions adapted to snappingly engage one or more corresponding recesses formed within said coronal opening of said implant so as to create an audible/tactile feedback upon inserting said healing cap into the implant.

3. The healing cap of claim 1, wherein said one or more resilient prongs and protrusions are adapted to apply a latent downward force to said healing cap when said healing cap is inserted into said implant.

4. The healing cap of claim 1 in combination with a dental implant adapted to matingly and snappingly receive said healing cap.

5. The healing cap of claim 1 wherein said distal end is adapted to completely cover said top surface of said implant when said healing cap is inserted into said implant.

6. The healing cap of claim 1 in combination with a removal tool comprising one or more prongs adapted to be matingly and snappingly received in said indentation of said healing cap.

7. The healing cap of claim 6, wherein said one or more prongs are resilient.

8. The healing cap of claim 6, wherein said one or more prongs are not resilient.

9. The healing cap of claim 6, wherein said one or more prongs of said removal tool are adapted such that a first removal force is required to remove said one or more prongs from said indentation after said removal is inserted into said healing cap.

10. The healing cap of claim 9, wherein said one or more resilient prongs and protrusions of said healing cap are adapted such that a second removal force is required to remove said healing cap from said implant after said healing cap is inserted into said implant, said first removal force being greater than said second removal force.

11. The healing cap of claim 1, wherein said healing cap is made of plastic.

12. A healing cap for covering a top surface of an implant installed in a patient's jawbone, the healing cap comprising a proximal end and a distal end, said proximal end being configured with one or more resilient prongs adapted to be inserted into a coronal opening formed in said implant and to snappingly engage and secure said healing cap to said implant, wherein said one or more resilient prongs are made of plastic and said distal end is made of a material other than plastic.

13. The healing cap of claim 12, wherein said distal end is made of at least one of a group consisting of titanium, stainless steel and ceramic.

14. A healing cap for covering a top surface of an implant installed in a patient's jawbone, said healing cap comprising a first end adapted to be snappingly mated to said implant and comprising a second end adapted to completely cover said top surface of said implant, wherein said distal end is configured with an indentation having an neck with a diameter smaller than a diameter of a lower portion of said indentation.

15. A The impression healing cap of claim 14, wherein said first end includes one or more of resilient prongs including one or more protrusions adapted to snappingly engage one or more corresponding recesses formed within a coronal opening of said implant so as to create an audible/tactile feedback upon inserting said healing cap into the implant.

16. The healing cap of claim 14, wherein said first end includes one or more resilient prongs and one or more protrusions that are adapted to apply a latent downward force to said healing cap when said healing cap is inserted into said implant.

17. The healing cap of claim 14 wherein combination with a dental implant adapted to matingly and snappingly receive said first end of said healing cap.

18. The healing cap of claim 14 in combination with a removal tool comprising one or more prongs adapted to be matingly and snappingly received in said indentation.

19. The healing cap of claim 18, wherein said one or more prongs of said removal tool are resilient.

20. The healing cap of claim 18, wherein said one or more prongs of said removal tool are not resilient.

21. The healing cap of claim 18, wherein said one or more prongs of said removal tool are adapted such that a first removal force is required to remove said one or more prongs from said indentation after said removal tool is inserted into said healing cap.

22. The healing cap of claim 21, wherein said one or more resilient prongs and protrusions of said healing cap are adapted such that a second removal force is required to remove said healing cap from said implant after said healing cap is inserted into said implant, said first removal force being greater than said second removal force.

23. The healing cap of claim 14, wherein said healing cap is made of plastic.

24. A healing cap for covering a top surface of an implant installed in a patient's jawbone, said healing cap comprising a first end adapted to be snappingly mated to said implant and comprising a second end adapted to completely cover said top surface of said implant, wherein said first end is made of plastic and said second end is made of a material other than plastic.

25. The healing cap of claim 24, wherein said second end is made of at least one of a group consisting of titanium, stainless steel and ceramic.

26. A healing cap for covering a top surface of a dental implant installed in a patient's mouth, said healing cap being snappingly mated to said implant and comprising a cover portion for covering a coronal opening and a top surface of said implant, wherein said cover portion includes an indentation having a neck with a diameter smaller than a diameter of a lower portion of said indentation.

27. The impression healing cap of claim 26, wherein said healing cap is mated to said implant by one or more of resilient prongs comprising one or more protrusions adapted to snappingly engage one or more corresponding recesses formed within said coronal opening of said implant.

28. The healing cap of claim 26, wherein said one or more resilient prongs and protrusions are adapted to apply a latent downward force to said healing cap when said healing cap is inserted into said implant.

29. The healing cap of claim 26 in combination with a removal tool comprising one or more prongs adapted to be matingly and snappingly received in said indentation.

30. The healing cap of claim 29, wherein said one or more prongs of said removal tool are resilient.

31. The healing cap of claim 29, wherein said one or more prongs of said removal tool are not resilient.

32. The healing cap of claim 29, wherein said one or more prongs of said removal tool are adapted such that a first removal force is required to remove said one or more prongs from said indentation of said healing cap after said removal tool is inserted into said healing cap.

33. The healing cap of claim 32, wherein said healing cap is mated to said implant by one or more of said resilient prongs comprising one or more protrusions adapted to snappingly engage one or more corresponding recesses formed within said coronal opening of said implant, wherein said one or more resilient prongs and protrusions of said healing cap are adapted such that a second removal force is required to remove said healing cap from said implant after said healing cap is inserted into said implant, said first removal force being greater than said second removal force.

34. The healing cap of claim 26, wherein said healing cap is made of plastic.

35. A healing cap for covering a top surface of a dental implant installed in a patient's mouth, said healing cap being snappingly mated to said implant and comprising a cover portion for covering a coronal opening and a top surface of said implant, wherein said healing cap is mated to said implant by one or more resilient prongs being made of plastic and said cover portion is made of a material other than plastic.

36. The healing cap of claim 35, wherein said cover portion is made of at least one of a group consisting of titanium, stainless steel and ceramic.

37. A healing cap for covering a top surface of an implant installed in a patient's jawbone, the healing cap comprising a proximal end and a distal end, said proximal end being sized and adapted to be inserted within a coronal opening formed in said implant, said healing cap further comprising resilient snap means for snappingly engaging corresponding surfaces formed within the coronal opening of said implant, said distal end comprising an cover portion adapted to cover the top surface of said implant, further comprising snap receiving means for snappingly engaging one or more prongs of a removal tool.

38. The healing cap of claim 37, wherein said healing cap is made of plastic.

39. A healing cap for covering a top surface of an implant installed in a patient's jawbone, the healing cap comprising a proximal end and a distal end, said proximal end being sized and adapted to be inserted within a coronal opening formed in said implant, said healing cap further comprising resilient snap means for snappingly engaging corresponding surfaces formed within the coronal opening of said implant, said distal end comprising in cover portion adapted to cover the top surface of said implant, wherein said resilient snap means are made of plastic and said cover portion is made of a material other than plastic.

40. The healing cap of claim 39, wherein said cover portion is made of at least one of a group consisting of titanium, stainless steel and ceramic.

41. A removal tool for removing a healing cap that is snappingly mated to a dental implant installed in a patient's mouth, said removal tool including a handle and one or more prongs adapted to be matingly and snappingly received in an indentation of said healing cap, wherein said one or more prongs are resilient.

42. A removal tool for removing a healing cap that is snappingly mated to a dental implant installed in a patient's mouth, said removal tool including a handle and one or more prongs adapted to be matingly and snappingly received in an indentation of said healing cap, wherein said one or more prongs of said removal tool are adapted such that a first removal force is required to remove said one or more prongs from said indentation after said removal tool is inserted into said healing cap and said first removal force is greater than a second removal force that is required to remove said healing cap from said implant after said healing cap is snappingly mated to said implant.

43. A method of installing and removing a healing cap for covering a top surface of an implant installed in a patient's jawbone, comprising:

inserting a proximal end of said healing cap into a coronal opening of said implant until said proximal end snappingly engages and secures said healing cap to said implant by applying a latent downward force on said implant, inserting a snapping portion of a removal tool into a top portion of said healing cap such that a first removal force which is greater than a second removal force required to remove said healing cap from said implant is required to remove said removal tool from said top portion;

separating said healing cap from said implant by moving said removal tool away from said implant.

\* \* \* \* \*